United States Patent
Hamers et al.

(10) Patent No.: US 9,708,716 B2
(45) Date of Patent: Jul. 18, 2017

(54) METHODS AND SYSTEMS FOR THE REDUCTION OF MOLECULES USING DIAMOND AS A PHOTOREDUCTION CATALYST

(71) Applicant: Wisconsin Alumni Research Foundation, Madison, WI (US)

(72) Inventors: Robert John Hamers, Madison, WI (US); Di Zhu, Madison, WI (US); Nigel Hajj Becknell, Ellicott City, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 304 days.

(21) Appl. No.: 14/585,444

(22) Filed: Dec. 30, 2014

(65) Prior Publication Data

US 2015/0299870 A1    Oct. 22, 2015

Related U.S. Application Data (63) Continuation of application No. 13/362,819, filed on Jan. 31, 2012, now Pat. No. 8,986,532.

(51) Int. Cl.
| | | |
|---|---|---|
| *C25B 1/00* | (2006.01) | |
| *C01B 31/18* | (2006.01) | |
| *C07C 1/02* | (2006.01) | |
| *C01C 1/02* | (2006.01) | |
| *B01J 19/12* | (2006.01) | |

(Continued)

(52) U.S. Cl.
CPC ............ *C25B 1/003* (2013.01); *B01J 19/123* (2013.01); *B01J 19/127* (2013.01); *B01J 21/18* (2013.01); *B01J 35/004* (2013.01); *B01J 37/18* (2013.01); *C01B 21/1409* (2013.01); *C01B 31/18* (2013.01); *C01C 1/02* (2013.01); *C07C 1/02* (2013.01); *B01J 27/24* (2013.01); *C07C 2101/16* (2013.01); *Y02P 20/52* (2015.11)

(58) Field of Classification Search
CPC ......... C25B 1/003; B01J 37/18; B01J 35/004; B01J 21/18; B01J 19/127; B01J 19/123; B01J 27/24; C01B 21/1409; C01B 31/18; C01C 1/02; C07C 1/02; C07C 2101/16
USPC ........................................ 205/340
See application file for complete search history.

(56) References Cited

U.S. PATENT DOCUMENTS

2001/0047980 A1* 12/2001 McNallan ............... B01J 37/24
                                                          216/75

FOREIGN PATENT DOCUMENTS

JP          2001089887 A  *  4/2001

OTHER PUBLICATIONS

Machine translation of JP 2001-089887 A.*

* cited by examiner

*Primary Examiner* — Keith Hendricks
*Assistant Examiner* — Colleen M Raphael
(74) *Attorney, Agent, or Firm* — Bell & Manning, LLC (57) ABSTRACT

Methods for the photoreduction of molecules are provided. The methods use diamond having a negative electron affinity as a photocatalyst, taking advantage of its ability to act as a solid-state electron emitter that is capable of inducing reductions without the need for reactants to adsorb onto its surface. The methods comprise illuminating a fluid sample comprising the molecules to be reduced and hydrogen surface-terminated diamond having a negative electron affinity with light comprising a wavelength that induces the emission of electrons from the diamond directly into the (Continued)

fluid sample. The emitted electrons induce the reduction of the molecules to form a reduction product.

6 Claims, 4 Drawing Sheets

(51) Int. Cl.
*B01J 37/18* (2006.01)
*C01B 21/14* (2006.01)
*B01J 21/18* (2006.01)
*B01J 35/00* (2006.01)
*B01J 27/24* (2006.01)

METHODS AND SYSTEMS FOR THE REDUCTION OF MOLECULES USING DIAMOND AS A PHOTOREDUCTION CATALYST

CROSS-REFERENCE TO RELATED APPLICATIONS

The present application is a continuation of U.S. patent application Ser. No. 13/362,819 that was filed Jan. 31, 2012, the entire contents of which are hereby incorporated by reference.

REFERENCE TO GOVERNMENT RIGHTS

This invention was made with government support under 0911543 and 0520527 awarded by the National Science Foundation. The government has certain rights in the invention.

BACKGROUND

The reduction of small molecules, such as nitrogen and carbon dioxide, is extraordinarily difficult because the one-electron reduction processes often involve high-energy intermediates. For example, in the fixation of nitrogen (conversion of $N_2$ to $NH_3$), the reaction $N_2+e^-\rightarrow N_2^-$ involves such high energy that the gas-phase anion $N_2^-$ exists only as a fleeting transient. The standard reduction potential for the analogous solution-phase reaction $N_2+e^- \rightarrow N_2^-{}_{(aq)}$ has been estimated at −4.2 V vs. the normal hydrogen electrode (NHE). While some evidence exists for formation of $N_2^-$ species at surfaces of ionic oxides such as MgO, nitrogen reduction is usually accomplished by coupling with the transfer of one more protons. Yet, even these have high energy; the reaction $N_2+H^++e^-\rightarrow N_2H$, has a calculated reduction potential $E°$ of −3.2 V vs. the normal hydrogen electrode (NHE).

The photocatalytic reduction of nitrogen was first discovered by Schrauzer and Guth (G. N. Schrauzer, T. D. Guth, *Journal of the American Chemical Society* 99, 7189 (1977)), who showed that $N_2$ could be reduced to $NH_3$ on the surface of $TiO_2$ powder when illuminated with light from a mercury arc lamp. Although since then various modified $TiO_2$ catalysts have been developed, the overall efficiency of the reaction remains poor. The poor efficiency arises because the proton-coupled reactions have relatively complicated pathways, and because the highly stable $N_2$ molecule has only a very low binding affinity for surfaces.

SUMMARY

Methods for the photoreduction of molecules are provided. The methods use diamond having a negative electron affinity as a photocatalyst, taking advantage of its ability to act as a solid-state electron emitter that is capable of inducing reductions without the need for reactants to adsorb onto its surface.

In one basic embodiment, the method comprises illuminating a fluid sample comprising the molecules to be reduced and hydrogen surface-terminated diamond having a negative electron affinity with light comprising a wavelength that induces the emission of electrons from the diamond directly into the fluid sample, wherein the emitted electrons induce the reduction of the molecules to form a reduction product. Once produced, the reduction product can be separated from the fluid sample and collected.

The methods can be used to reduce a variety of molecules, including small molecules, such as $N_2$, $CO_2$, CO, $NO_x$ and aromatic molecules that include one or more benzene rings.

Also provided are reaction systems for carrying out the methods. In one embodiment the reaction system comprises a reduction cell comprising a fluid sample comprising the molecules to be reduced and hydrogen surface-terminated diamond having a negative electron affinity; and a light source configured to illuminate at least a portion of the reduction cell with light comprising a wavelength capable of inducing the emission of electrons from the diamond into the fluid sample to induce the reduction of the molecules to form a reduction product. The system may further include a reduction product collection cell configured to collect the reduction product emitted from the reduction cell.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described.

DETAILED DESCRIPTION

Methods and systems for the photocatalytic reduction of molecules are provided. The methods utilize the ability of hydrogen-terminated diamond surfaces to act as solid-state electron emitters able to induce reduction reactions.

Figure 1:
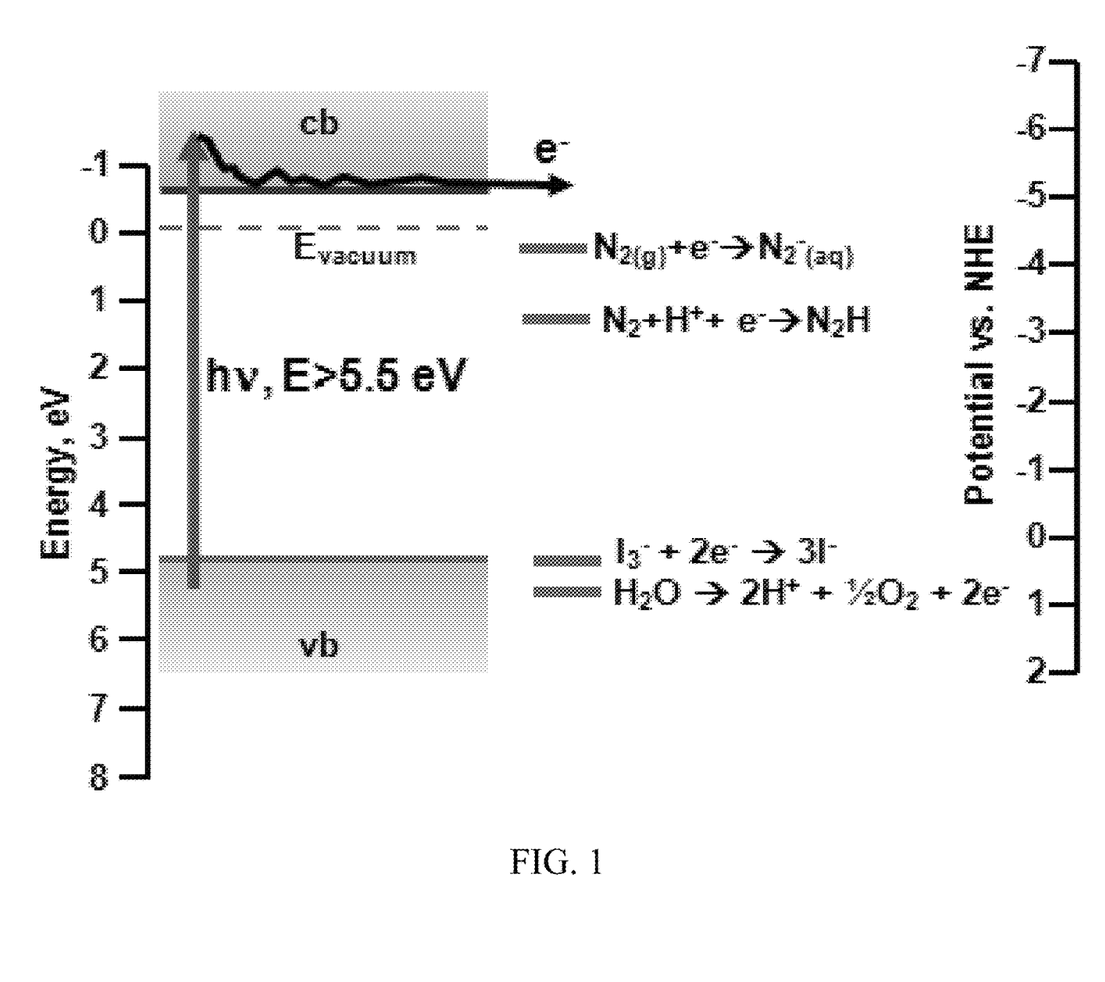
FIG. 1 is an electronic energy-level diagram showing the valence band (vb) and conduction band (cb) of H-terminated diamond and several relevant electrochemical reduction potentials, including both the absolute energy scale (left) and the electrochemical energy scale (right) relative to the normal hydrogen electrode (NHE).

Diamond is a wide-bandgap semiconductor with a bandgap of 5.5 eV. When the surface of diamond is terminated with hydrogen atoms, the conduction-band energy lies ~0.8-1.3 eV above the "vacuum level", which represents the energy of a free electron with zero kinetic energy. This property is termed 'negative electron affinity' (NEA). One consequence of NEA is that when H-terminated diamond surfaces are illuminated with light with photon energies hv greater than the bandgap, electrons that are excited to the conduction band in the bulk can be directly emitted into vacuum with no barrier. In effect, diamond becomes a direct solid-state emitter of electrons with energy equal to the conduction band of diamond. When placed on an electrochemical energy scale, as depicted in FIG. 1, (using 4.44 eV as the absolute energy of the NHE) the emitted electrons have a reduction potential of approximately −5.5 Volts vs. NHE. The high energy combined with diamond's NEA makes it possible for illuminated diamond surfaces to emit electrons directly into adjacent reactants, thereby eliminating the need for reactant molecules to adsorb onto the surface in order to perform photochemical reduction reactions. In effect, the NEA property allows one to bring electrons to the reactants, rather than having to bring the reactants to the source of the electrons. Moreover, the high energy level of emitted electrons makes it feasible to initiate very high-energy reduction processes.

One embodiment of the present methods comprises illuminating a fluid sample comprising the molecules to be reduced and the hydrogen surface-terminated diamond having a negative electron affinity with light comprising a wavelength that induces the emission of electrons from the diamond into the fluid sample. The emitted electrons induce the reduction of the molecules to form a reduction product which can be separated from the fluid sample and collected.

The present methods can be used to reduce a variety of molecules, such as those capable of reduction via a one-electron reduction process or those that undergo proton-coupled electron transfer processes. The methods are particularly well-suited for the reduction of small molecules whose one-electron reduction processes involve high-energy intermediates. Reduction reactions that can be carried out using the present methods include, but are not limited to, the reduction of $N_2$ to $NH_3$ or hydrazine ($N_2H_4$); the reduction of $CO_2$ to CO, or organic molecules such as methane ($CH_4$), formaldehyde ($H_2CO$) or methanol ($CH_3OH$), and the reduction of nitrogen oxides ($NO_x$, i.e., NO and $NO_2$) to $N_2$. Other molecules that can be reduced using the present methods include benzene ring-containing organic molecules of the type that are reducible via Birch reduction. Examples of such molecules include substituted and unsubstituted benzene and naphthalene.

The reductions may be single-step reductions or multiple (e.g., two or more) step reductions. For example, the present methods can be used to reduce $CO_2$ to CO, which can be further reduced to other reduction products, such as $CH_4$, $H_2CO$ and/or $CH_3OH$. Alternatively, the intermediate reduction products in a multiple-step reduction scheme can themselves be used as the starting product in a single-step reduction. For example, rather than starting with $CO_2$, CO can be used as a starting product in a single-step reduction scheme for the production of $CH_4$, $H_2CO$ and/or $CH_3OH$.

For the purposes of this disclosure, the term diamond refers to carbon materials, wherein the carbon atoms are primarily $sp^3$ hybridized, and includes species of diamond having varying degrees of crystallinity. Suitable carbon materials having $sp^3$ hybridization ≥50% include microcrystalline diamond, nanocrystalline diamond, ultrananocrystalline diamond and diamond-like materials, such as tetrahedral amorphous carbon (ta-C).

The diamond may be doped or undoped. Undoped diamond has a strong absorption in the UV region of the electromagnetic spectrum. In embodiments where the diamond is doped, the dopants can be used to enhance the absorption of light in the visible and/or near UV regions of the spectrum, thereby providing a higher photocatalytic activity per unit area. The dopants can be p-type dopants, such as boron (B) atoms, or n-type dopants, such as phosphorus (P) atoms or nitrogen (N) atoms.

Nitrogen-doped diamond may be particularly well-suited for use in the present methods because previous studies have shown that electrons can be field-emitted from nitrogen-doped diamond at very low energies, and that these electrons are emitted from the conduction band rather than that valence band. (K. Okano, S. Koizumi, S. R. P. Silva, and G. A. J. Amaratunga, Nature (London) 381, 140 (1996); H. Yamaguchi, T. Masuzawa, S. Nozue, Y. Kudo, I. Saito, J. Koe, M. Kudo, T. Yamada, Y. Takakuwa, and K. Okano, Phys. Rev. B 80, 165321 (2009).) Consequently, electrons may be emitted from nitrogen-doped diamond using longer wavelengths, including visible light. Recently Nemanich, et al. have reported that electrons can be emitted from nitrogen-doped diamond into vacuum using visible-light wavelengths of 340-550 nm. (T. Y. Sun, F. A. M. Koeck, C. Y. Zhu, and R. J. Nemanich, Applied Physics Letters, Volume: 99 Issue: 20 Article Number: 202101 DOI: 10.1063/1.3658638 Published: Nov. 14, 2011.) Consequently, the use of diamond doped with nitrogen or other n-type dopants such as phosphorus may be useful in providing photocatalytic activity using visible light instead of ultraviolet light.

The diamond can be provided in the form of a powder that forms a suspension in the fluid sample. Suitable diamond powders include those with nominal average particle sizes in the range from about 100 nm to about 300 nm. Although, powders with particles sizes outside of this range can also be used. Alternatively, the diamond can be coated or loaded on a support substrate to provide a diamond electrode that can be immersed in the fluid sample. In yet another design, a diamond electrode is itself formed entirely from diamond. The diamond can be a high-quality, electronics-grade diamond. However, such high quality diamond is not required. Lower grade diamond, including relatively inexpensive diamond grit can also be used.

The fluid of the fluid sample in which the reductions are carried out will typically be a liquid or supercritical fluid. In some embodiments, the fluid is the liquid or supercritical fluid form of a reduction reactant. For example, in the reduction of $CO_2$, the fluid of the fluid sample can be liquid $CO_2$ or supercritical $CO_2$. In other embodiments, the fluid of the fluid sample comprises a solvent for the molecules to be reduced. Examples of liquid media that can provide a solvent for the molecules to be reduced and/or other reactants include water, aqueous solutions or organic solvent-based solutions. Suitable organic solvents include those in which the molecules to be reduced have significant solubility. Examples of suitable organic solvents include propylene carbonate (PC), dimethyl formamide (DMF) and methanol, in which $CO_2$ has substantial solubility. In addition, it is advantageous if the solvent is able to stabilize the solvated electrons emitted from the diamond. An example of an organic solvent in which solvated electrons are very stable is hexamethylphosphoric triamide (HMPA). The molecules to be reduced can be introduced into the fluid along with other reactants, such as $H_2$. Gaseous reactants can be introduced into the fluid by flowing or bubbling them through the fluid sample. In some embodiments the fluid sample is saturated with the reactant in order to maximize the product yield.

The reduction reactions can be carried out in a system comprising a reduction cell; a light source configured to illuminate at least a portion of the reduction cell with light;

and a reduction product collection cell configured to collect reduction product emitted from the reduction cell. In this system, the reduction cell comprises a fluid sample comprising the reactant molecules to be reduced and the hydrogen surface-terminated diamond having a negative electron affinity. The light source is selected to emit radiation having a wavelength capable of inducing the emission of electrons from the diamond into the fluid sample where they induce the reduction of the reactant molecules to form a reduction product. Generally, the light source will be an ultraviolet light source that emits light with wavelengths of about 230 nm (corresponding to the 5.5 eV bandgap energy of diamond) or lower. If visible light is used wavelengths of, for example, ≤550 nm may be used (e.g., wavelengths in the range from about 440 to about 550 nm). However, if doped diamond is utilized, it may be advantageous to use a light source that emits across one or more of the UV, near-UV and visible regions of the electromagnetic spectrum. Broadband light sources, such as Xe arc lamps and HgXe arc lamps are suitable. Optionally, filters can be used to filter out unwanted radiation, such as infrared radiation.

In embodiments where a diamond electrode is utilized, a counter electrode can also be immersed in the liquid sample. In such embodiments, a voltage source in electrical communication with the electrodes can be used to apply a voltage between the diamond electrode and the counter electrode. This small voltage can help 'push' the electrons into the liquid sample and away from the diamond electrode after they are emitted. The applied voltage is desirably small (e.g., ≤2 V) such that it does not interfere with the photocatalytic nature of the reduction process.

In some embodiments, the reduction system includes a single reduction cell geometry, while in other embodiments an H-cell geometry is used. In the single reduction cell geometry, the diamond in the reduction cell has no external electrical connection and, therefore, must induce both oxidation and reduction reactions in order to achieve charge neutrality. In the H-cell geometry a diamond electrode is immersed in the fluid sample in a first reduction cell and a counter electrode (e.g., a platinum electrode) that is electrically connected to the diamond electrode is immersed in an oxidation medium is a second cell (the oxidation cell). In this geometry the fluid sample and the oxidation medium are in electrical contact but do not mix and the oxidation and reduction reactions are separated.

Once the reduction product is formed, it can be separated from the fluid sample and captured. For example, gas phase reduction product molecules will be generated as a gaseous effluent that can be collected in a collection cell after it escapes the fluid sample.

EXAMPLES

Example 1

This example demonstrates the use of hydrogen-terminated diamond as a photoreduction catalyst for the reduction of $N_2$ to $NH_3$.

Materials and Methods:
Samples:
Three different types of diamond were investigated. Electrochemistry grade boron-doped diamond (Product 145-500-0030) and electronic-grade polycrystalline diamond plates (Product 145-500-0005) were purchased from Element Six, Inc. Natural diamond powder was purchased from Microdiamant AG, Lengwil Switzerland, 125 nm nominal average diameter, product NAT 0-0.25. In each case the diamond samples were hydrogen-terminated before use as described below.

Hydrogen-Termination:
Solid substrates: Hydrogen-termination of solid diamond substrates followed procedures outlined by Thoms, et al. (B. D. Thoms, M. S. Owens, J. E. Butler, C. Spiro, *Applied Physics Letters*. 65, 2957 (1994)). Samples were loaded in a custom-fabricated hydrogen plasma chamber constructed from a 2-inch quartz tube surrounded by radio-frequency coils connected to a 13.56 MHz radio-frequency (RF) power source via an impedance-matching circuit. The tube was repeatedly evacuated and purged with hydrogen gas, and then heated to approximately 800° C. in 5.0 Torr of flowing $H_2$. An RF plasma was ignited with a delivered power of 35 Watts for 20 minutes. The samples were cooled in the plasma for 15 min and then further cooled in pure hydrogen for 20 min.

Diamond powder: diamond powder was loaded in a metal boat and then heated at 1023 K in a 1 atmosphere of flowing $H_2$ for 3 hours in a tube furnace with a quartz tube liner. The sample was then cooled down to room temperature in hydrogen. Diffuse reflectance infrared spectroscopy measurements showed that this treatment removed surface oxides and left the diamond powder hydrogen-terminated.

SEM Imaging of Powdered Diamond and $TiO_2$:
Scanning electron microscopy images of the diamond and $TiO_2$ powders were obtained by spin-coating dilute suspensions onto a silicon substrate and then imaging in a Leo Supra55 VP scanning electron microscope. The SEM images of the diamond powder showed a substantial dispersion in sizes, with an average of approximately 125 nm, in agreement with the manufacturer's specifications. The $TiO_2$ nanopowder had particles with a narrower size distribution and an average diameter of approximately 100 nm.

Photocatalytic Measurements of Nitrogen Reduction to Ammonia:
Photocatalytic efficiency measurements were performed using a high-pressure mercury lamp (Daiel Instrument, model#66921), located approximately 10 inches from the samples. A water absorptive filter was used to eliminate infrared radiation. Pure $N_2$ gas was slowly bubbled through the quartz reaction vessel (the reduction cell), which contained deionized water (the fluid of the fluid sample) that was saturated with $N_2$ via a continuous slow flow. The gas-phase effluent was passed into a second quartz vessel (the collection cell) containing diluted $H_2SO_4$ to capture the $NH_3$ produced for later analysis. The $NH_3$ in both the reactant vessel and the capture vessel were measured as described below, almost all the $NH_3$ was found in the capture vessel.

The production of ammonia was measured using the indophenols blue method (D. F. Boltz, Ed., *Colorimetric Determination of Nonmetals*, (J. Wiley and Sons, New York, 1978)). A 2 ml aliquot of solution was removed from the reaction vessel. To this solution was added 0.100 ml of a 1M NaOH solution containing 5% salicylic acid and 5% sodium citrate (by weight), followed by addition of 20 µl of 0.05 M NaClO and 20 µl of an aqueous solution of 1% (by weight) Na[Fe(NO)(CN)$_5$] (sodium nitroferri cyanide). After 1 hour, the absorption spectrum was measured using a Shimadzu 2401PC Ultraviolet-Visible Spectrophotometer. The formation of indophenols blue was determined using the absorbance at a wavelength of 700 nm. Absolute calibration of the method was achieved using ammonium chloride solutions of known concentration as standards.

X-Ray Photoelectron and Ultraviolet Photoemission Spectroscopy Measurements:

X-ray photoelectron spectroscopy (XPS) data were obtained using a modified Physical Electronics system equipped with an aluminum $K_\alpha$ source, a quartz-crystal X-ray monochromator, and a 16-channel detector array. Ultraviolet photoemission spectroscopy (UPS) measurements were performed using the same apparatus, using excitation from a He(I) resonance lamp. The electron affinities were calculated from the energy width (w) of the emission spectrum and the known photon energy (21.2 eV) and diamond bandgap (5.5 eV) using $\chi = E_{photon} - E_{gap} = 21.2 - 5.5 - w$.

Figure 2:
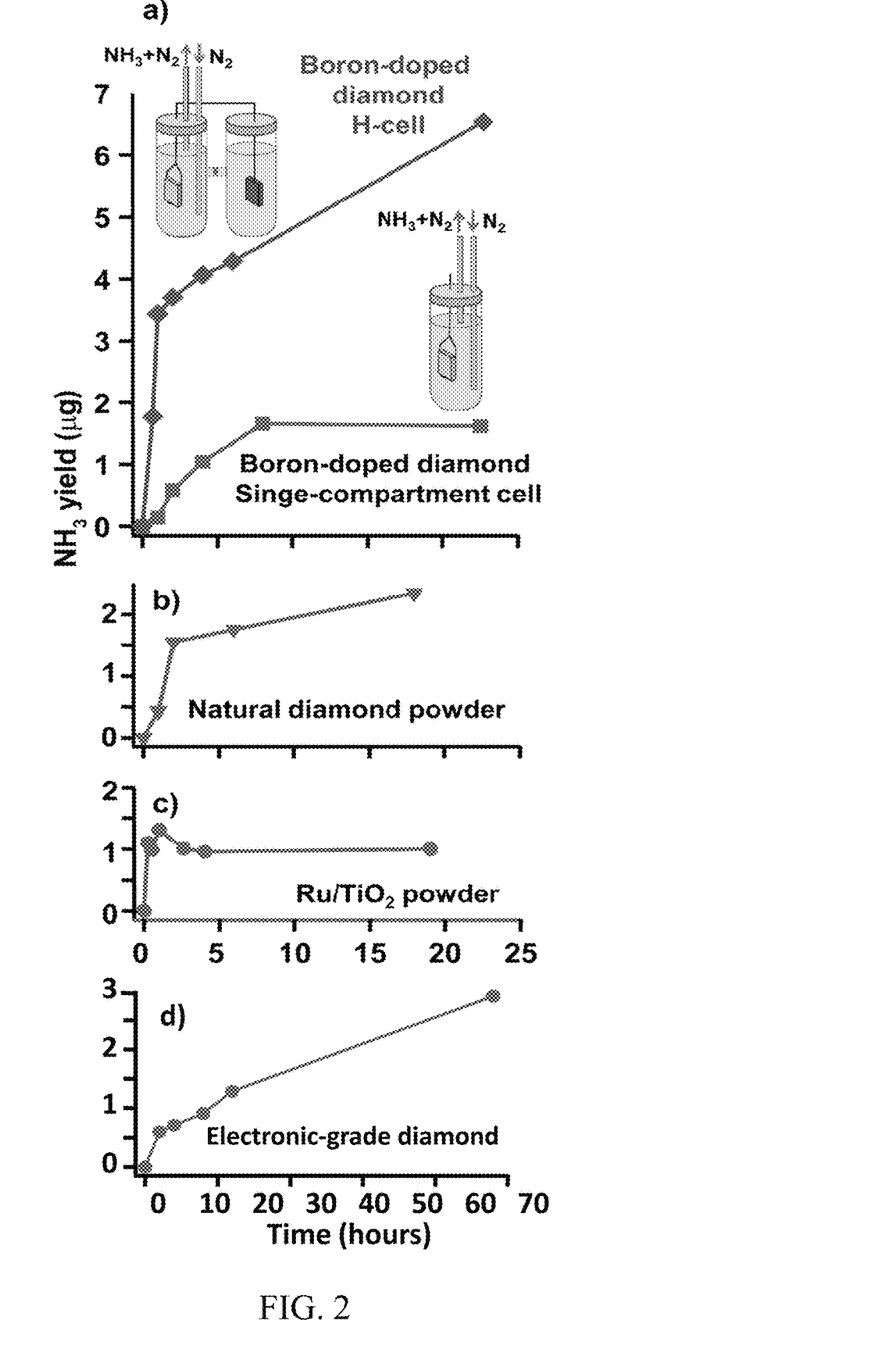
FIG. 2 shows graphs of the total ammonia yield from the photoreduction of $N_2$: a) boron-doped electrochemical grade diamond in an H-cell and a single-cell measured in $N_2$-saturated water; (b) natural diamond powder, c) $Ru/TiO_2$ and d) electronic-grade diamond.

Results:

FIG. 2 shows the ammonia produced when each of the diamond samples was placed into $N_2$-saturated deionized water and illuminated with light from a high-pressure HgXe arc lamp for the indicated periods of time. For the boron-doped sample results are shown for experiments using a single-compartment cell and an H-cell design. In the single-compartment cell the diamond sample has no external electrical connection and therefore must induce both oxidation and reduction reactions in order to maintain charge neutrality. In the H-cell geometry the diamond electrode is contained in one compartment (the reduction cell), and a second compartment (the oxidation cell) contains a platinum electrode immersed in a 0.001 M solution of KI in water. The solutions in the two compartments were connected via a glass frit that provided electrical contact between the solutions but prevented mixing, and an external wire connected the diamond and Pt electrodes. In this geometry the diamond need only induce the $N_2$ reduction, while charge neutrality is maintained by oxidation of $I^-$ to $I_3^-$ at the Pt electrode.

In both the stand-alone and H-cell geometries, the boron-doped diamond sample induced a rapid increase in $NH_3$ production over the first several hours, followed by a slower rate at longer times. Three types of control experiments were also performed: (1) no illumination, (2) illumination of the sample with Ar replacing the $N_2$, and 3) illumination of the water without a diamond sample present. These controls all showed no significant production of $NH_3$.

As shown in FIG. 2a, the rate of $NH_3$ production for the boron-doped diamond was increased several-fold by separating the oxidation and reduction reactions via the H-cell design. This increase occurred because the valence band of diamond is relatively shallow (see FIG. 1) making the corresponding valence-band holes relatively poor oxidizing agents. The standard electrochemical reduction potential for the reaction $O_2(g) + 4H^+ + 4 e^- \rightarrow 2H_2O$ is $E^0 = 1.229$ V, so that at pH=7 the potential needed to oxidize water is E=+0.82 V. This is close to, or possibly even slightly more positive than, the position of the valence band of diamond. However, when illuminated with photons with hv>5.5 eV the emission of electrons makes the diamond positively charged, increasing its potential until the conduction band can induce water oxidation at a rate equivalent to that of the electron emission. Thus, in the single-cell geometry the rate at which nitrogen can be reduced to $NH_3$ is limited by the need for an oxidation process.

By providing a sacrificial moiety such as $I^-$ that can be more easily oxidized, the reduction reaction can proceed at a faster rate because the Pt electrode can rapidly oxidize $I^-$ to $I_3^-$ as necessary to maintain charge neutrality. While this could also be accomplished in a single cell, the H-cell avoids interaction of the reaction products and eliminates losses due to absorption of light by the $I^-$ solution (KI is colorless, but it absorbs UV strongly). Similar results were also achieved replacing the Pt electrode with $Cu^{2+}$, using the reaction $Cu^{2+} + 2 e^- \rightarrow Cu_{(s)}$ ($E^0 = +0.34$ V) as the oxidation reaction; this yielded results identical to those using F.

FIG. 2d shows that the ability of H-terminated diamond to induce photocatalytic reduction of $N_2$ to $NH_3$ also extends to high-quality electronic-grade diamond and, remarkably, even to inexpensive diamond powder of the type commonly used as a polishing compound (FIG. 2b), when dispersed in water (~125 nm average size, 0.1 wt % suspension, stirred). Because the diamond powder and electronic grade diamond are non-conductive, results for these samples were obtained only in the single-compartment cell.

As a point of comparison the photocatalytic activity of ruthenium-loaded $TiO_2$ catalyst was also measured. This catalyst was prepared using the impregnation method using a Ru loading of 0.24% by weight, which previous studies showed yielded the highest activity for nitrogen reduction (K. T. Ranjit, T. K. Varadarajan, B. Viswanathan, *Journal of photochemistry and Photobiology A: Chemistry* 96, 181 (1996)). FIG. 2c shows the total yield of $NH_3$ production after a dispersion (0.1% in water, stirred) was illuminated under conditions identical to those used for the diamond studies. While the Ru/$TiO_2$ sample showed good activity initially, it was rapidly deactivated and showed little detectable activity after ~15 minutes. Comparison of the data from diamond samples in FIGS. 2a-2b with that from the Ru/$TiO_2$ sample in FIG. 2c showed that the diamond samples were able to produce significantly more $NH_3$. The loss of activity of Ru/$TiO_2$ and other metal-activated $TiO_2$ catalysts has been noted in many previous studies and has been attributed to a number of factors, including re-oxidation of the ammonia into nitrate or nitrite ions by the photoexcited holes of $TiO_2$ and the loss of special surface sites able to bind $N_2$ to the catalyst surface. (K. Tennakone, S. Wickramanayake, C. A. N. Fernando, O. A. Ileperuma, S. Punchihewa, *Journal of the Chemical Society, Chemical Communications*, 1078 (1987); Q.-s. Li, K. Domen, S. Naito, T. Onishi, K. Tamaru, Chemistry letters, 321 (1983).) Diamond can provide higher activity both because the barrier-free photoemission of electrons into the reactant liquid obviates the need for $N_2$ adsorption to the surface, and also because the shallower valence band of diamond makes it less likely to re-oxidize the products of the reduction.

To establish a correlation between the ammonia yield and the excitation wavelength, the same configuration as in FIG. 2 was used, except that absorptive filters were included to limit the range of excitation wavelengths. These data, shown in FIG. 3, demonstrated that high activity was observed only when using short-wavelength light, with wavelengths $\lambda \leq 230$ nm, corresponding to the bandgap of diamond. Longer wavelengths contributed only minimally to $N_2$ reduction. Given that the photocatalytic activity of diamond is only induced by very short-wavelength photons, it was remarkable that when both were illuminated with broad-spectrum light diamond still provided a higher yield than Ru/$TiO_2$, which absorbs a much larger fraction of the incident light ($\lambda \leq 390$ nm). The dark control sample showed no detectable ammonia; the value shown represents the detection limit of the indophenol method.

Figure 3:
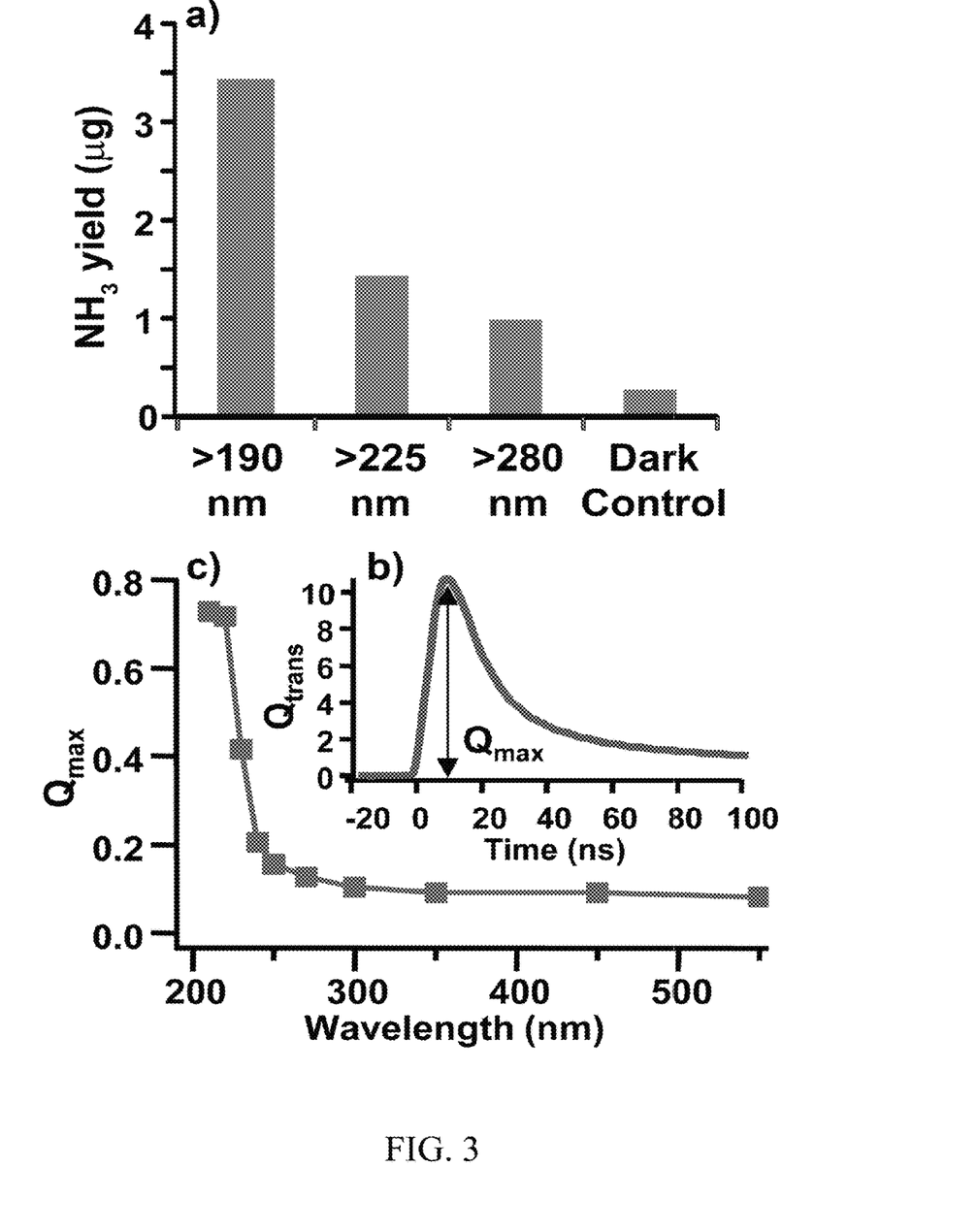
FIG. 3 shows (a) the ammonia yield from boron-doped diamond in an H-cell after illumination for 1 hour, using absorptive filters to limit the range of incident radiation; (b) the time-resolved electron emission from boron-doped diamond into $N_2$-saturated deionized water when illuminated at 210 nm at room temperature; and c) the wavelength dependence of the electron emission, normalized by wavelength to yield an effective wavelength-dependent photoemission efficiency.

The photoelectrochemical response of the diamond-water interface was characterized using transient surface photovoltage (SPV) measurements. In these measurements, the sample was illuminated with pulsed laser (3 ns pulse width); emission of electrons or other separation of charge induced a transient photocurrent that was measured using a second, capacitively coupled electrode placed ~25 μm away; integration of the current yielded the amount of charge transfer, $Q_{trans}$. FIG. 3a showed the time evolution of $Q_{trans}$ (inset) and the magnitude of the maximum ($Q_{max}$) as a function of wavelength for a boron-doped diamond in contact with $N_2$-satured water. The wavelength-dependent measurements were normalized by photon energy. The sign of the charge transfer in FIG. 3A corresponds to an accumulation of negative charges at the diamond-water interface. The wavelength dependence shows that at wavelengths $\lambda>270$ nm there was very low response, while as the wavelength was reduced below 270 nm the emissive properties increased rapidly and then saturated at $\lambda<230$ nm. This profile is very similar to that reported previously for diamond photoemission in to vacuum (J. B. Cui, J. Ristein, L. Ley, *Physical Review B* 60, 16135 (December, 1999)). A small amount of signal was observed at wavelengths longer than ~300 nm; this likely arose from optically induced transitions involving defects and/or impurities within the sample, which is dark in color due to the presence of a small amount of graphitic impurities.

Figure 4:
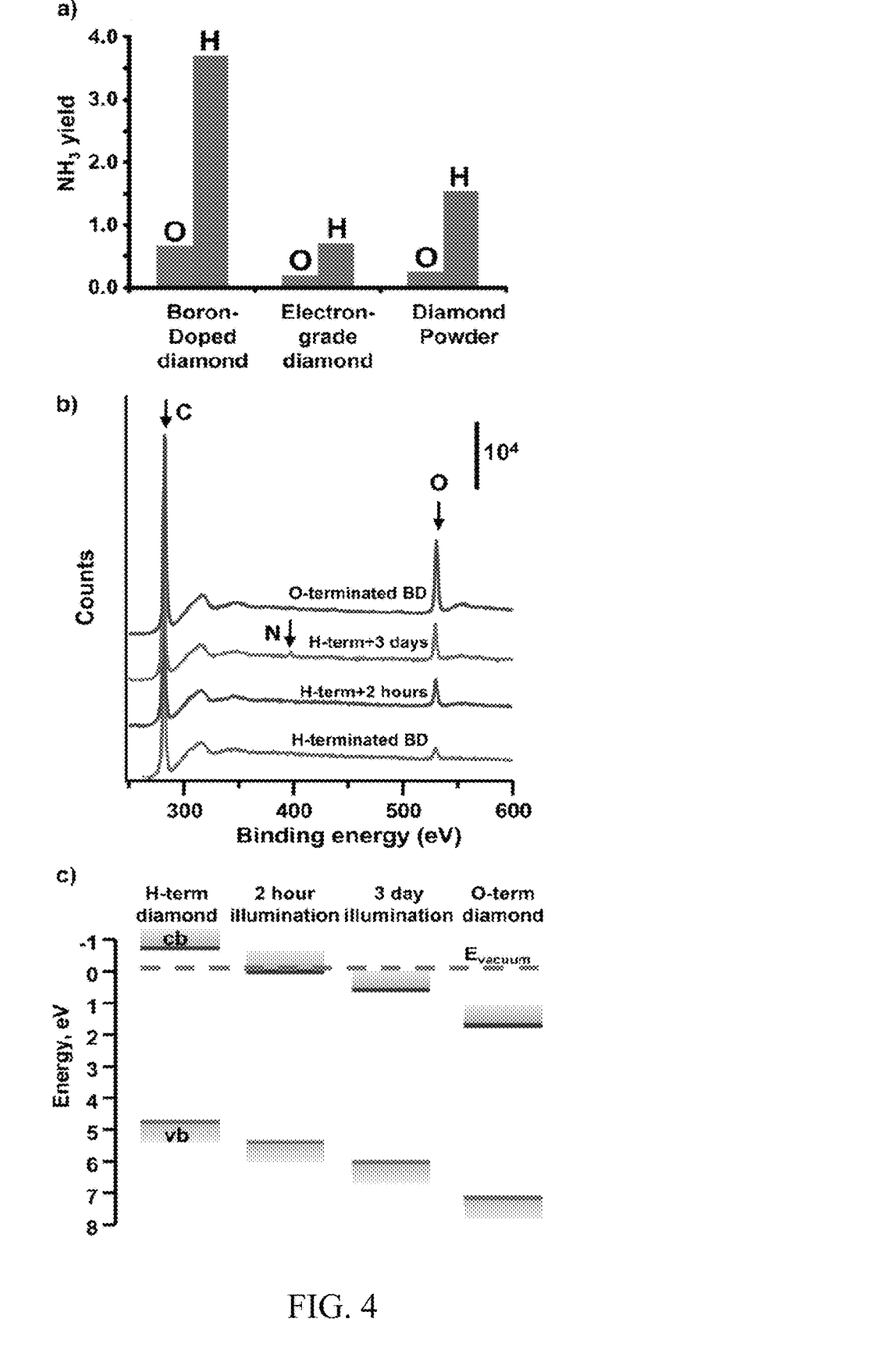
FIG. 4 shows (a) a comparison of $NH_3$ yield from H-terminated and O-terminated diamond samples, measured after illumination for 2 hours; (b) a comparison of XPS spectra of H-terminated and O-terminated boron-doped diamond illuminated for 2 hours and for 3 days; and (c) the position of the valence bands (vb) and the conduction bands (cb) of boron-doped diamond as determined by ultraviolet photoemission spectroscopy measurements, showing a transition from negative electron affinity to positive electron affinity.

The significance of diamond's negative electron affinity was illustrated by comparing the reactivity of diamond with different surface terminations. While H-terminated surfaces have NEA, oxidized diamond surfaces have positive electron affinity (PEA) because the dipoles associated with the C—O surface bonds induce a barrier to electron emission; consequently, the photoemissive properties of diamond are greatly attenuated when oxidized. To demonstrate the influence of surface termination on the photocatalytic reduction of $N_2$, H-terminated samples were compared with samples that had been intentionally oxidized by exposure to ozone produced by short-wavelength (185 nm) ultraviolet light in air, leaving them O-terminated. FIG. 4A shows the relative yield of ammonia produced by H-terminated and O-terminated samples of high-quality electronic-grade diamond, boron-doped electrochemical grade diamond, and diamond powder, measured after 2 hours illumination in water. In all three cases the H-terminated surfaces had high photocatalytic activity, while the oxidized surfaces showed much lower reactivity. These results show excitation of electrons to the conduction band alone was not sufficient to get good activity—it is also necessary for the electrons to have an efficient pathway for emission from the diamond to the adjacent reactant liquid, which is greatly facilitated by the negative electron affinity of the H-terminated samples.

While H-terminated diamond retains its photocatalytic activity for several days of constant illumination, the activity was gradually reduced. FIG. 4b shows X-ray photoelectron spectroscopy data from boron-doped diamond samples after various illumination times in water; these show that the initially H-terminated sample can undergo a gradual increase in surface oxygen and also the appearance of a small amount of surface nitrogen (400.6 eV, typical of amino groups) only in very long-time illuminated samples.

The electron affinity from equivalent samples was measured using valence-band photoemission spectroscopy. As shown in FIG. 4c, the H-terminated sample had negative electron affinity, $\chi \sim -0.8$ V, while the fully oxidized sample has a positive electron affinity of ~1.5 V. The crossover from negative to positive electron affinity occurred after approximately 2 hours of illumination. This suggests that the observed decrease in catalytic efficiency after illumination for more than several hours is a direct consequence of a gradual loss of NEA due to oxidation of the surface.

Example 2

This example demonstrates the use of hydrogen-terminated diamond as a photoreduction catalyst for the reduction of $CO_2$ to CO.

Materials and Methods:
Samples:
Natural diamond powder was purchased from Microdiamant AG, Lengwil Switzerland. The diamond powder had a nominal average particle size of 150 to 250 nm. The diamond powder was suspended in 0.1 M KCl and 0.1 mM $Na_2SO_3$ solution with nanopure water. In each case the diamond samples were hydrogen-terminated before use as described below.

Hydrogen-Termination:
The diamond powder was hydrogen terminated by heating at 750° C. under a hydrogen atmosphere for two hours. Approximately 20 mg of H-terminated diamond powder was sonicated in 20 mL of this solution for 15 minutes.

Photocatalytic Measurements of Carbon Dioxide Reduction to Carbon Monoxide:
The diamond suspension (approximately 15 mL) was then placed in a quartz vial, sealed with septum, and stirred while $CO_2$ (99.999% purity) was bubbled through for 30 minutes. The septum was then removed and the glass vial was placed on an infrared gas cell. The gas cell had calcium fluoride windows on it, sealed with black wax. An FTIR spectrum of the cell was taken. Then, the quartz vial with the diamond suspension was irradiated with deep ultraviolet radiation from a xenon lamp through a water filter. The irradiation took place after 18 hours. The diamond suspension was stirred continuously.

Results:
FTIR spectra of the sample before and after irradiation showed that initially only $CO_2$ was present in the solution, but after irradiation CO was also present. Control experiments were conducted to confirm the result.

In the first control experiment, a sample was run with the same amount of the hydrogen-terminated diamond powder in KCl/$Na_2SO_3$ solution, but without exposure to UV radiation. Once the diamond was suspended in the salt solution the quartz vial was wrapped in foil to prevent any light from entering. After bubbling with $CO_2$ for 30 minutes, the vial was attached to the infrared gas cell and the suspension was stirred for 43 hours. FTIR spectra were taken at 0 hours and at 43 hours. No CO peak was observed in the spectra before or after the period of stirring.

In the second control experiment, a sample of the salt solution without the diamond was run. In this experiment $CO_2$ was bubbled through the salt solution in a quartz vial for 30 minutes. The vial was attached to the FTIR gas cell and the $CO_2$ solution was irradiated with deep UV radiation for 18 hours. No CO peak was present in the spectra before or after the irradiation.

Example 3

This example demonstrates the use of nitrogen-doped, hydrogen-terminated diamond as a photoreduction catalyst for the reduction of $N_2$ to $NH_3$.

Materials and Methods:
Samples:
Samples of nitrogen-doped diamond were obtained from Applied Diamond, Inc. (Wilmington, Del.).

Ammonia Production Using Nitrogen-Doped Diamond:
After hydrogen-termination, the diamond (0.5 cm×0.5 cm) was placed in a quartz tube and flushed with 50 standard cubic centimeters per minute (sccm) ultrahigh purity nitrogen. The area of the nitrogen-doped diamond was smaller than that of the diamond samples used in Examples 1 and 2 (e.g., 0.25 $cm^2$ area compared with 1 $cm^2$ for the other samples).

Results:

The amount of ammonia produced per unit area of illuminated diamond was approximately 5-6 times higher than that produced by the boron-doped diamond or electronic-grade diamond, indicating that nitrogen-doped diamond had higher photocatalytic efficiency than the other forms of diamond.

The data for the measured ammonia yield over a period of four hours of illumination are shown in Table 1.

TABLE 1

| Time (h) | Ammonia Yield (µg) |
|---|---|
| 0 | 0 |
| 1 | 0.22 |
| 3 | 1.18 |
| 4 | 1.34 |

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for the photoreduction of molecules, the method comprising:
    (a) illuminating a fluid sample comprising the molecules to be reduced and a hydrogen surface-terminated diamond electrode having a negative electron affinity with light comprising a wavelength that excites electrons from the valence band of the diamond to the conduction band of the diamond, thereby inducing the emission of the excited electrons from the diamond into the fluid sample, wherein the emitted excited electrons induce the reduction of the molecules to form a reduction product, further wherein substantially all of the reduction product is formed via the emitted excited electrons; and
    (b) collecting the reduction product,
    wherein a counter electrode is immersed in the fluid sample.

2. The method of claim 1, wherein a voltage source is in electrical communication with the hydrogen surface-terminated diamond electrode and the counter electrode.

3. The method of claim 2, further comprising applying a voltage between the hydrogen surface-terminated diamond electrode and the counter electrode.

4. The method of claim 3, wherein the applied voltage is sufficient to move the emitted excited electrons away from the hydrogen surface-terminate diamond electrode.

5. The method of claim 3, wherein the voltage is less than or equal to 2 V.

6. A method for the photoreduction of molecules, the method comprising:
    (a) illuminating a fluid sample comprising the molecules to be reduced and a hydrogen surface-terminated diamond electrode having a negative electron affinity with light comprising a wavelength that excites electrons from the valence band of the diamond to the conduction band of the diamond, thereby inducing the emission of the excited electrons from the diamond into the fluid sample, wherein the emitted excited electrons induce the reduction of the molecules to form a reduction product; and
    (b) collecting the reduction product,
    wherein a counter electrode is immersed in the fluid sample and further wherein the hydrogen surface-terminated diamond electrode is free of silicon.

* * * * *